US00PP31343P2

(12) United States Plant Patent
Hansen

(10) Patent No.: US PP31,343 P2
(45) Date of Patent: Jan. 7, 2020

(54) ***DELOSPERMA* PLANT NAMED 'FIG FUSION'**

(50) Latin Name: ***Delosperma* hybrid**
Varietal Denomination: Fig Fusion

(71) Applicant: Christopher M. Hansen, Zeeland, MI (US)

(72) Inventor: Christopher M. Hansen, Zeeland, MI (US)

( * ) Notice: Subject to any disclaimer, the term of this patent is extended or adjusted under 35 U.S.C. 154(b) by 0 days.

(21) Appl. No.: 16/350,511

(22) Filed: Nov. 26, 2018

(51) Int. Cl.
*A01H 5/02* (2018.01)
*A01H 6/00* (2018.01)

(52) U.S. Cl.
USPC ..... Plt./422
CPC ..... *A01H 6/00* (2018.05)

(58) Field of Classification Search
USPC ..... Plt./422
See application file for complete search history.

*Primary Examiner* — Anne Marie Grunberg
(74) *Attorney, Agent, or Firm* — Penny J. Aguirre

(57) ABSTRACT

A new cultivar of *Delosperma* plant named 'Fig Fusion' that is characterized by that is characterized by its floriferous blooming habit, its hot pink flowers, its very compact and tight mounds of foliage that do not become long or leggy during the summer growing months, its strong re-blooming habit during the entire growing season and into late fall, its small plant size, its uniform rooting habit, and its uniform blooming period with other plants in the series.

1 Drawing Sheet

Botanical classification: *Delosperma* hybrid.
Variety denomination: 'Fig Fusion'.

CROSS REFERENCE TO RELATED APPLICATIONS

This application is co-pending with U.S. Plant patent Applications filed for plants derived from the same breeding program that are entitled *Delosperma* Plant Named 'Banana Blast' (U.S. Plant patent application Ser. No. 16/350,513), *Delosperma* Plant Named 'Coconut Crush' (U.S. Plant patent application Ser. No. 16/350,512), *Delosperma* Plant Named 'Pumpkin Perfection' (U.S. Plant patent application Ser. No. 16/350,509), *Delosperma* Plant Named 'Saucy Strawberry' (U.S. Plant patent application Ser. No. 16/350,514), and *Delosperma* Plant Named 'Tangerine Tango' (U.S. Plant patent application Ser. No. 16/350,510).

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant less than one year prior to the effective filing date would have been obtained from a direct or indirect disclosure from the Inventor under 35 U.S.C. 102(b)(1).

BACKGROUND OF THE INVENTION

The present invention relates to a new and distinct cultivar of *Delosperma* plant of hybrid origin, botanically known as *Delosperma* 'Fig Fusion' and will be referred to hereinafter by its cultivar name, 'Fig Fusion'. The new cultivar of *Delosperma* is a hardy herbaceous perennial grown for use as a landscape and container plant and is particularly suitable as a groundcover.

'Fig Fusion' arose from an ongoing breeding program by the Inventor in Hudsonville, Mich. The objective was to obtain a new series of *Delosperma* cultivars with more floriferous blooming habits, smaller and more compact and uniform plant habits, and blooming periods that are the same amongst all cultivars in the series when grown under the same conditions.

The Inventor made a controlled cross in July of 2014 in his test garden in Hudsonville, Mich. between an unnamed proprietary plant from the Inventor's breeding program, reference no. 288-6, as the female parent and pollen that was pooled from unnamed proprietary plants of *Delosperma* as the male parent. The exact male parent is therefore unknown. The Inventor selected 'Fig Fusion' as a single unique plant in June of 2016 from the resulting seedlings.

Asexual reproduction of the new cultivar was first accomplished by tip stem cuttings in April of 2015 in Hudsonville, Mich. Asexual propagation by tip stem cuttings has determined the characteristics to be stable and reproduced true to type in successive generations.

SUMMARY OF THE INVENTION

The following traits have been repeatedly observed and are determined to be the characteristics of the new cultivar. These attributes in combination distinguish 'Fig Fusion' as a unique cultivar of *Delosperma*.

1. 'Fig Fusion' exhibits a floriferous blooming habit with an average of 47 flowers per plant as a 10-week-old plant grown in a 1-quart container started from a 128-cell plug.
2. 'Fig Fusion' exhibits hot pink flowers.
3. 'Fig Fusion' exhibits very compact and tight mounds of foliage that do not become long or leggy during the summer growing months.
4. 'Fig Fusion' exhibits strong re-blooming during the entire growing season and into late fall.

5. 'Fig Fusion' exhibits a small plant size reaching an average of 3.8 cm in height and 38 cm in width.
6. 'Fig Fusion' exhibits uniform rooting occurs in just 10 days.
7. 'Fig Fusion' exhibits a uniform blooming period with other plants in the series.

The seed parent plant of 'Fig Fusion', no. 288-6, differs from 'Fig Fusion' in having a 30% taller plant habit, 55% less flowers and flowers that are pastel pink in color. 'Fig Fusion' can be most closely compared to the cultivars 'Jewel of Desert Rosequartz' (U.S. Plant Pat. No. 23,452) and 'WOWDRW5' (U.S. Plant Pat. No. 25,572). 'Jewel of Desert Rosequartz' is similar to 'Fig Fusion' in flower color and a flowering period. 'Jewel of Desert Rosequartz' differs from 'Fig Fusion' in having less flowers; an average of 33 flowers per 10-week old plant, smaller flowers, a taller plant height, and a less floriferous re-bloom in fall. 'WOWDRW5' is similar to 'Fig Fusion' in having a similar blooming period during the summer. 'WOWDRW5' differs from 'Fig Fusion' in having flowers that are 20% larger in size, less flowers; an average of 38 flowers per 10-week old plant, a taller plant height, and flowers that have a white center. 'Fig Fusion' can also be compared to cultivars with co-pending patent applications from the same breeding program that have the same blooming periods. 'Coconut Crush' differs from 'Fig Fusion' in having white flowers, 'Banana Blast' differs from 'Fig Fusion' in having yellow flowers, 'Pumpkin Perfection' differs from 'Fig Fusion' in having orange flowers, 'Saucy Strawberry' differs from 'Fig Fusion' in having red-pink flowers, and 'Tangerine Tango' differs from 'Fig Fusion' in having red-orange flowers.

BRIEF DESCRIPTION OF THE DRAWING

The following is a detailed description of the new cultivar as observed on a 3-month-old plant of 'Fig Fusion' as grown outdoors in a two-quart container in Hudsonville, Mich. The photograph provides a view of 'Fig Fusion' in bloom. The colors in the photograph may differ slightly from the color values cited in the detailed botanical description, which accurately describe the colors of the new *Delosperma*.

DETAILED BOTANICAL DESCRIPTION

The following is a detailed description of 3-month-old plants of the new cultivar as grown outdoors in 9-cm containers outdoors in Hudsonville, Mich. The phenotype of the new cultivar may vary with variations in environmental, climatic, and cultural conditions, as it has not been tested under all possible environmental conditions. The color determination is in accordance with the 2015 Colour Chart of The Royal Horticultural Society, London, England, except where general color terms of ordinary dictionary significance are used.

General description:

*Blooming period.*—Blooms heavily from June 1 through late July, then re-blooms through late October in Michigan.

*Plant type.*—Herbaceous perennial.

*Plant habit.*—Clumping, tightly mounded, compact ground cover.

*Plant type.*—Herbaceous perennial.

*Plant habit.*—Clumping, tightly mounded, compact ground cover.

*Height and spread.*—An average of 6 cm in height and about 21 cm in diameter.

*Hardiness.*—Observed to at least U.S.D.A. Zones 6 to 9.

*Diseases and pests.*—No susceptibility or resistance to diseases or pests has been observed.

*Root description.*—Fibrous, 199A in color.

*Root development.*—Cuttings root uniformly in 128-cell plugs in 6 weeks, 128-cell planted into a 9-cm pot or quart pot will finish and be in full bloom at 9 to 10 weeks after planting.

*Propagation.*—Stem tip cuttings.

*Growth habit.*—Moderate.

Stem description:

*Shape.*—Round.

*Stem color.*—Young stems; 145B, older stems 152A.

*Stem size.*—An average of 3.5 cm in length and 1 mm in diameter.

*Internode length.*—An average of 1 to 4 mm.

*Stem substance.*—Succulent, lower older stems become slightly woody.

*Stem surface.*—Young; moderately glossy and glabrous, mature is woody.

*Stem strength.*—Young; moderately strong, mature; strong.

*Branching habit.*—Freely and very densely branching, both basal and lateral, 3 to 5 lateral branches per basal stem, 20 basal stems per plant (growing just above the soil).

Foliage description:

*Leaf shape.*—Ligulate, oblong and narrow.

*Leaf substance.*—Succulent, thick.

*Leaf division.*—Simple.

*Leaf base.*—Cuneate.

*Leaf apex.*—Acute.

*Leaf venation.*—Not visible.

*Leaf margins.*—Entire.

*Leaf arrangement.*—Opposite to whorled.

*Leaf surface* (*upper and lower surface*).—Densely pubescent with very short glandular hairs; too small to measure.

*Leaf color.*—Young and mature leaves; base 144B blending upward and becoming 143A.

*Leaf size.*—About 3 cm in length and 4 mm in width.

*Leaf quantity.*—Average of 15 per lateral branch.

*Leaf attachment.*—Sessile.

Inflorescence description:

*Inflorescence type.*—Flowers solitary, terminal.

*Flower number.*—Densely floriferous, quantity ranges, 3 to 4 per lateral stem.

*Flower fragrance.*—None.

*Flower aspect.*—Mostly held upright.

*Flower longevity.*—A few days, self-cleaning.

*Flower type.*—Single.

*Flower size.*—Average of 1.5 cm in diameter and 9 mm in depth.

*Flower buds.*—Broadly ovate to oblong in shape, an average of 1 cm in depth and 6 mm in diameter, color; 143A, surface is densely pubescent with minute hairs that match surface color.

*Calyx.*—Rotate in shape, average of 2 mm in depth and 4 mm in diameter.

*Sepals.*—5, rotate, narrowly ovate in shape, margin entire, an average of 5 mm in length and 2 mm in width, acute apex, cuneate base, both surfaces glossy and densely covered with soft pubescence that matches the surface color, inner and outer surface is 143A in color, texture is thick and succulent.

*Petals.*—An average of 28 per flower, rotate and slightly curved upward, narrowly oblanceolate in shape, surface is smooth and glossy on both surfaces, margin entire, apex acute to bluntly acute, base cuneate, an average of 7 mm in length and 1 mm in width, color; opening and fully open flowers upper surface; base 157C, mid-section 76B, blending out to the tip N75A, end of tip 77A, when exposed to direct sunlight the color changes to include hues of N74C throughout the petals, opening and fully open flowers lower surface; N75A, very edge of tip N80A.

*Petaloids.*—An average of 14 per flower, rotate, curved downward over petals, surrounding stamens, lanceolate in shape, moderately to highly glossy on both surfaces, margin entire, apex acute, base cuneate, an average of 4 mm in length and 0.75 mm in width, color upper and lower surface; 84C.

*Peduncle.*—Average of 2.5 cm in length and 1 mm in diameter, held in multiple angles, surface is glossy, densely covered with minute pubescence matching surface color, color; 149A, maturing peduncles slightly flushed with 166A.

*Pedicel.*—None.

Reproductive organs:

*Pistils.*—5, an average of 1 mm in length, pistil, style and stigma are not distinguishable, triangular shaped, 143A in color, ovary is 142B in color.

*Stamens.*—Average 30, anthers; dorsifixed and narrowly oblong in shape, an average of 0.5 mm in diameter, 21A in color, filaments are up to 3 mm in length 10D in color, pollen is high in quantity and 21A in color.

*Fruit.*—Fruit and seed production was not observed under the conditions tested.

It is claimed:

1. A new and distinct variety of *Delosperma* plant named 'Fig Fusion' as described and illustrated herein.

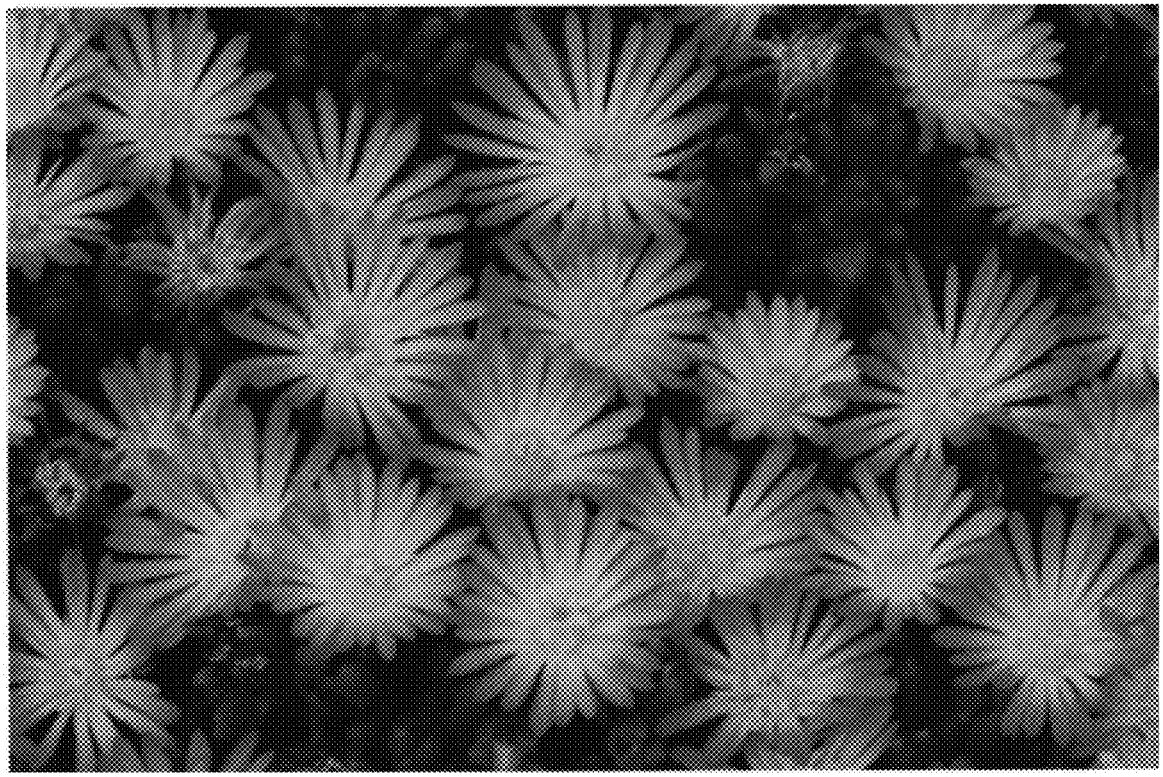

* * * * *